(12) United States Patent
Madsen et al.

(10) Patent No.: US 7,581,541 B2
(45) Date of Patent: Sep. 1, 2009

(54) MULTILUMEN TRACHEAL CATHETER

(75) Inventors: Edward B. Madsen, Riverton, UT (US); Scott M. Teixeira, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 426 days.

(21) Appl. No.: 11/198,994

(22) Filed: Aug. 8, 2005

(65) Prior Publication Data

US 2007/0028925 A1    Feb. 8, 2007

(51) Int. Cl.
*A61M 16/04* (2006.01)
*A61M 16/20* (2006.01)

(52) U.S. Cl. .......................... 128/207.14; 128/207.16; 128/205.19; 128/204.24; 128/206.22; 128/912

(58) Field of Classification Search ............ 128/207.14, 128/207.15, 207.16, 204.18, 205.19, 912, 128/202.27; 604/118, 119, 93.01, 96.01, 604/101.03, 103.01, 103.02; 137/625.46, 137/876
See application file for complete search history.

(56) References Cited

U.S. PATENT DOCUMENTS

| | | | |
|---|---|---|---|
| 2,791,217 A | 5/1957 | Iskander | |
| 3,613,727 A * | 10/1971 | Orieux | 137/614.17 |
| 4,248,221 A | 2/1981 | Winnard | |
| 4,305,392 A * | 12/1981 | Chester | 604/98.01 |
| 4,584,998 A | 4/1986 | McGrail | |
| 4,607,635 A | 8/1986 | Heyden | |
| 4,637,389 A | 1/1987 | Heyden | |
| 4,840,173 A | 6/1989 | Porter, III | |
| 4,881,542 A | 11/1989 | Schmidt et al. | |
| 5,029,580 A * | 7/1991 | Radford et al. | 128/207.14 |
| 5,140,983 A | 8/1992 | Jinotti | |
| 5,143,062 A | 9/1992 | Peckham | |
| 5,201,310 A | 4/1993 | Turnbull | |
| 5,207,641 A * | 5/1993 | Allton | 604/32 |
| 5,279,549 A | 1/1994 | Ranford | |
| 5,311,864 A | 5/1994 | Huerta | |
| 5,328,456 A * | 7/1994 | Horiguchi et al. | 604/22 |
| 5,360,413 A | 11/1994 | Leason et al. | |
| 5,372,131 A | 12/1994 | Heinen, Jr. | |
| 5,488,949 A | 2/1996 | Kreifels et al. | |
| 5,490,503 A | 2/1996 | Hollister | |
| 5,582,167 A | 12/1996 | Joseph | |
| 5,687,714 A | 11/1997 | Kolobow et al. | |
| 5,803,078 A | 9/1998 | Brauner | |
| 5,819,723 A | 10/1998 | Joseph | |
| 5,832,920 A | 11/1998 | Field | |

(Continued)

FOREIGN PATENT DOCUMENTS

DE    2939794    4/1981

(Continued)

*Primary Examiner*—Justine R Yu
*Assistant Examiner*—Clinton Ostrup
(74) *Attorney, Agent, or Firm*—James B. Robinson; Scott B. Garrison

(57) ABSTRACT

A multilumen tracheal tube or catheter is disclosed. The tube has a plurality of suction lumens, each having a suction port. A rotatable suction port collar is provided. The suction port collar has an inlet and an outlet. The collar overlaps each suction port and is capable of selectively occluding a number of the suction ports while enabling unimpeded passage between a remainder of the ports and the outlet.

18 Claims, 5 Drawing Sheets

U.S. PATENT DOCUMENTS

| | | | |
|---|---|---|---|
| 5,845,634 A | 12/1998 | Parker | |
| D412,984 S | 8/1999 | Cover et al. | |
| 6,062,223 A | 5/2000 | Palazzo et al. | |
| 6,460,540 B1 | 10/2002 | Klepper | |
| 6,550,475 B1 | 4/2003 | Oldfield | |
| 6,612,304 B1* | 9/2003 | Cise et al. | 128/200.26 |
| 6,634,360 B1* | 10/2003 | Flodin | 128/207.14 |
| 6,668,821 B2* | 12/2003 | Christopher | 128/200.26 |
| 6,695,810 B2 | 2/2004 | Peacock, III et al. | |
| 6,796,309 B2 | 9/2004 | Nash et al. | |
| 6,895,966 B2* | 5/2005 | Christopher | 128/207.15 |
| 7,089,942 B1 | 8/2006 | Grey | |
| 2001/0050082 A1* | 12/2001 | Christopher | 128/207.15 |
| 2002/0014238 A1 | 2/2002 | Kotmel | |
| 2002/0077586 A1* | 6/2002 | Madsen et al. | 604/27 |
| 2003/0116162 A1* | 6/2003 | Madsen et al. | 128/207.14 |
| 2004/0011364 A1 | 1/2004 | Dhuper et al. | |
| 2004/0255951 A1 | 12/2004 | Grey | |
| 2005/0182291 A1 | 8/2005 | Hirata | |
| 2005/0229933 A1* | 10/2005 | McGrail et al. | 128/207.14 |
| 2006/0207602 A1 | 9/2006 | Kolobow et al. | |
| 2006/0260617 A1* | 11/2006 | Abolfathi et al. | 128/207.29 |
| 2007/0028924 A1* | 2/2007 | Madsen et al. | 128/207.15 |

FOREIGN PATENT DOCUMENTS

| | | |
|---|---|---|
| DE | 19734821 | 2/1999 |
| EP | 0766976 A2 | 4/1997 |
| GB | 2199630 | 7/1988 |
| GB | 2207736 | 2/1989 |
| JP | 2005177134 | 7/2005 |
| WO | WO 93/09833 | 5/1993 |
| WO | WO 99/38548 | 8/1999 |
| WO | WO 2005/009522 | 2/2005 |

* cited by examiner

MULTILUMEN TRACHEAL CATHETER

BACKGROUND

The present invention relates to a tracheal tube used for mechanical ventilation of a hospital patient, by insertion of the tube into the trachea of the patient. In particular, the present invention relates to a tracheal tube having means for irrigating and/or evacuating contaminated secretions accumulating above the tracheal tube cuff and thereby reducing the risk of such contaminated secretions entering the lungs of the patient.

Tracheal intubation involves the insertion of a tubular device, known as a tracheal tube, into the trachea of a patient. The tracheal tube passes through the trachea and terminates at a position above the carina, anterior to a position between the second and fourth thoracic vertebrate. Gases may then be introduced through the tracheal tube and into the lungs of the patient.

The primary purposes of tracheal intubation, are to mechanically ventilate the patient's lungs, when a disease prevents the patient from normal, breathing induced ventilation, or to apply anesthetic gases during surgical intervention. In order to create enough air pressure to accomplish such mechanical ventilation and to prevent escape of gases past the tube, it is necessary to seal the passageway around the tracheal tube. A seal may be produced by the use of an inflatable cuff formed integrally with and surrounding the tracheal tube. When the tracheal tube has been introduced into the patient's trachea, the inflatable cuff will normally be located about 3 to 5 centimeters above the carina and within the tube-like trachea.

The inflatable cuff is then inflated so as to engage the wall of the trachea and thereby seal the trachea and prevent gases being introduced through the tracheal tube from simply backing up around the tube. While treatment of this sort has proved successful for patients having chronic or acute respiratory diseases, there is a constant risk of several complications.

In particular, many patients receiving tracheal intubation develop pneumonia, resulting from an infection of the lungs, possibly induced by contaminated, pooled secretions entering the trachea and the lungs after bypassing the epiglottis during intubation. The epiglottis normally operates as a valve which selectively closes the entry into the trachea and lungs, to prevent the introduction of secretions and particulate matter. However, when a tracheal tube is in place, the epiglottis is held in an open position, and secretions which would normally be directed away from the trachea and into the digestive system, instead follow the path of the tracheal tube and pool above the inflatable cuff of the tracheal tube.

The greatest risk of such infectious secretions reaching the lungs is upon the cessation of mechanical ventilation. In particular, when the need for tracheal intubation ends, the inflatable cuff of the tracheal tube is deflated so that the tracheal tube may be withdrawn from the patient. The infectious secretions which have pooled above the inflatable cuff are then released and are free to flow into the lungs, where bronchitis or pneumonia may rapidly develop. There is also the risk of the infectious secretions reaching the lungs while intubated, by aspiration of the secretions past the tracheal tube cuff.

To overcome these risks, it is known in the prior art to combine a single lumen suction tube with a tracheal tube. The suction tube is joined to the tracheal tube in a suitable manner, the end of the suction tube terminating at a position above the inflatable cuff. The suction tube provides means for suction or evacuation of any pooled secretions which accumulate in the trachea above the inflatable cuff. However, such prior art devices have the disadvantage that use of a single lumen for the suction tube often causes direct suction to be exerted on the tracheal mucosa which may then result in damage to the mucosa.

U.S. Pat. No. 4,840,173 to Porter III, describes an endotracheal tube having a single lumen suction tube merged thereto. In particular, this patent describes a device wherein the suction tube is laminated to the outside of the ventilation tube, so that the suction tube terminates at a position just above the inflatable cuff. The suction tube includes multiple openings which may be used to evacuate secretions which pool above the inflatable cuff. In addition, the inflatable cuff includes a section immediately adjacent to the end of the suction tube that is less flexible than the rest of the inflatable cuff, to insure that the flexible material of the inflatable cuff is not sucked up against the suction tube openings. The endotracheal tube described in the Porter III patent has the disadvantages noted above, that the single lumen suction tube may exert suction on the tracheal mucosa and thereby cause damage to the mucosa. Further, the Porter III device is of a relatively complex design, requiring difficult processing, resulting in expensive production.

U.S. Pat. No. 5,143,062, issued to Peckham, discloses an endotracheal tube comprising a double lumen through which air may be circulated, creating an indirect gentle suction through a suction eye communicating with the distal ends of the lumens, and located at a position proximal to the inflation cuff. This design, however, does not provide adequate suction necessary for aspirating secretions and is easily occluded.

The above noted patent references fail to adequately address the suctioning of secretions which have pooled above the inflatable cuff in a manner that is sufficient to accomplish the task but is not so strong so as to cause damage to the mucosa. Moreover, these references and other conventional endotracheal and tracheal tubes lack the ability to suction these secretions, even when a patient is turned according to nationally instituted decubitus prevention protocols. That is, they fail to provide alternative suction capabilities in the event the patient is turned or in the event the desired suction lumen is occluded by secretions.

As the background devices fail to disclose a tracheal tube and suction catheter system having these structural characteristics, the need for such a device is apparent. The instant invention addresses this by providing a multilumen tracheal tube and suction catheter system comprising a device that enables the surgical team to direct suctioning to any number of lumens within the tracheal tube.

SUMMARY OF THE INVENTION

The present invention improves upon a tracheal tube. In one embodiment, a tube having a first wall and a second wall concentric to the first wall is provided. The first wall surrounds and defines a ventilation lumen which is adjacent to a first surface. The first wall may be attached at a second surface to a first surface of the second wall at a plurality of partitions. This enables a plurality of suction lumens to be defined by the second surface of the first wall, the first surface of the second wall, and surfaces of adjacent partitions. Each suction lumen would have a suction port formed through a portion of the second wall. A suction port collar having an inlet and an outlet is also provided. The collar surrounds the tube and overlaps the suction ports. The collar is selectively positionable so as to enable fluid communication between the inlet and at least one suction port while occluding any remaining suction port. The outlet of the suction port would be adapted to connect to a suction source.

In some embodiments, the suction port collar is rotatable about the tube. In other embodiments a guide may be provided. Such a guide may be coupled to the tube and disposed over each suction port, the guide would have openings aligned with each suction port, and the suction port collar would be rotationally attached to the guide. The collar may be configured as a cylindrical ring having an inner diameter, an outer diameter, and a tubular conduit affixed substantially normal to a plane tangential to the outer diameter.

The inlet to the collar is at that end of the conduit coincident with the inner diameter, and the outlet is at the opposite end of the conduit. The inlet may be capable of aligning with only a single suction port at any one point in time, a multiple of such suction ports, or no suction port.

In another embodiment, a tracheal tube having a plurality of suction lumens, each suction lumen having a suction port; and a suction port collar may be provided. The suction port collar may have an outlet and an inlet. The collar may overlap each suction port, a portion of the collar selectively occluding a number of the ports while enabling unimpeded passage between a remainder of the ports and the outlet. Such a tube may contain a ventilation lumen as well as suction lumens which are radially disposed about an outer diameter of the ventilation lumen. Each suction lumen may have an inlet and an outlet, the outlet corresponding to at least one of the suction ports. Such a tube may be provided with an inflatable cuff sealed to and surrounding the tube at a distal end adapted to seal the trachea of a patient. Each suction lumen would have an inlet port proximal to the inflatable cuff and terminate at one of the suction ports distal from the inflatable cuff.

Other objects, advantages and applications of the present invention will be made clear by the following detailed description of a preferred embodiment of the invention and the accompanying drawings wherein reference numerals refer to like or equivalent structures.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims. Those skilled in the art will appreciate that aspects of the various embodiments discussed may be interchanged and modified without departing from the scope and spirit of the invention.

Figure 1:
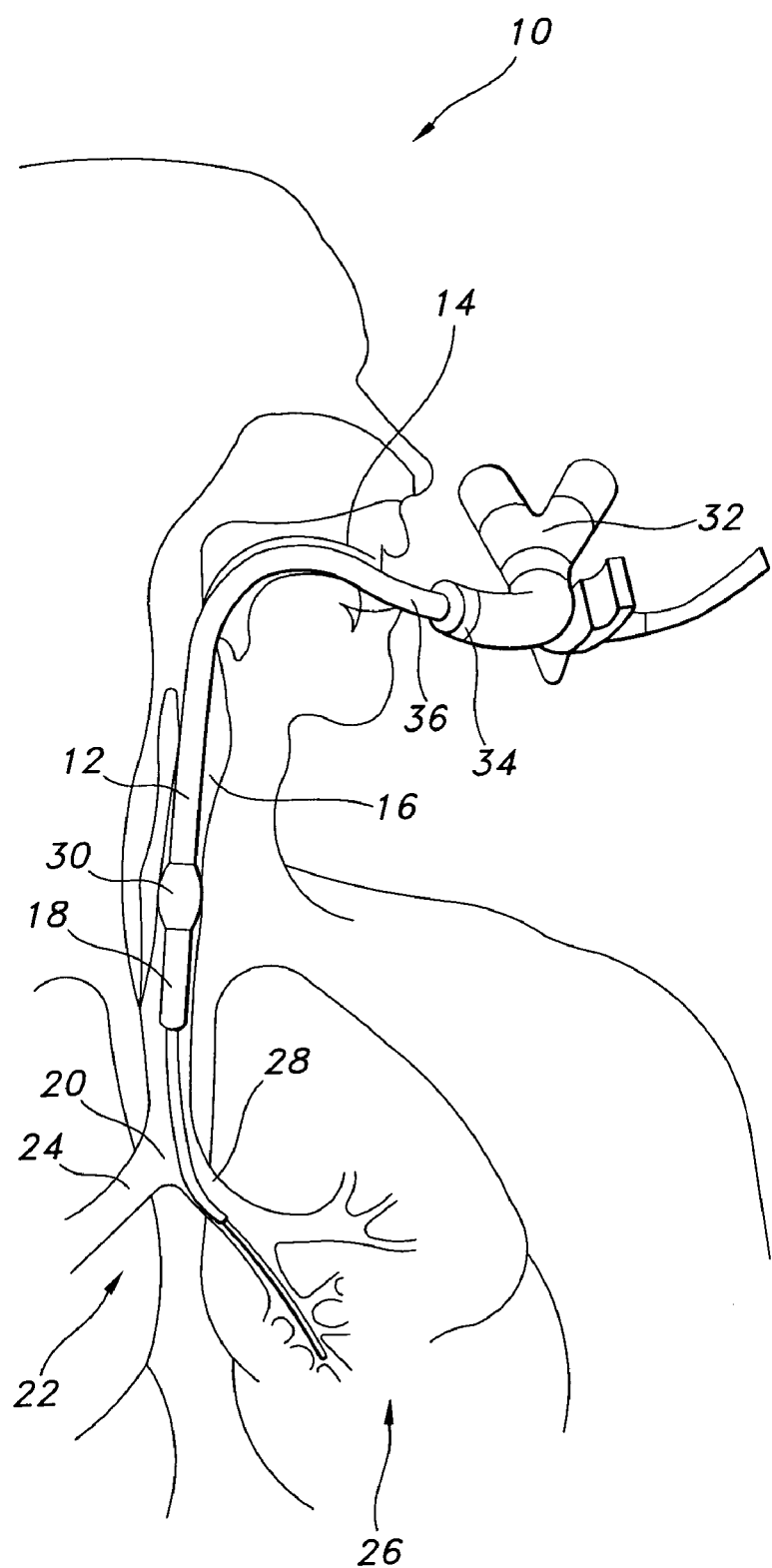
FIG. 1 is diagrammatic illustration of one embodiment of a multilumen catheter placed within a patient in accordance with the present invention.

Referring to FIG. 1, a tracheal tube 12 is depicted extending through the mouth 14 and the trachea 16 of the upper respiratory system of patient 10. The tracheal tube 10 terminates in a distal end 18 well above the point 20 at the first bifurcation of trachea 16 into the right lung 22 through the right mainstem bronchus 24 and into the left lung 26 through the left mainstem bronchus 28. Typical sub-branchings of the mainstem bronchus are shown in FIG. 1 for illustrative purposes in relation to the sub-branching of left mainstem bronchus 24 into left lung 26.

The distal end 18 of tracheal tube 12 is provided with a balloon 30 which, when inflated, engages the walls of trachea 16 to facilitate mechanical ventilation of patient lo through a connector 32 coupled to a standard tracheal tube adapter 34 at the proximal end 36 of tracheal tube 12. As would be understood by those of skill in the art, air from the ventilating apparatus for patient 10 enters tracheal tube 12 through one leg of the connector 32, and correspondingly, air is returned to the ventilating apparatus from patient 10 through a second leg of the connector.

Figure 2:
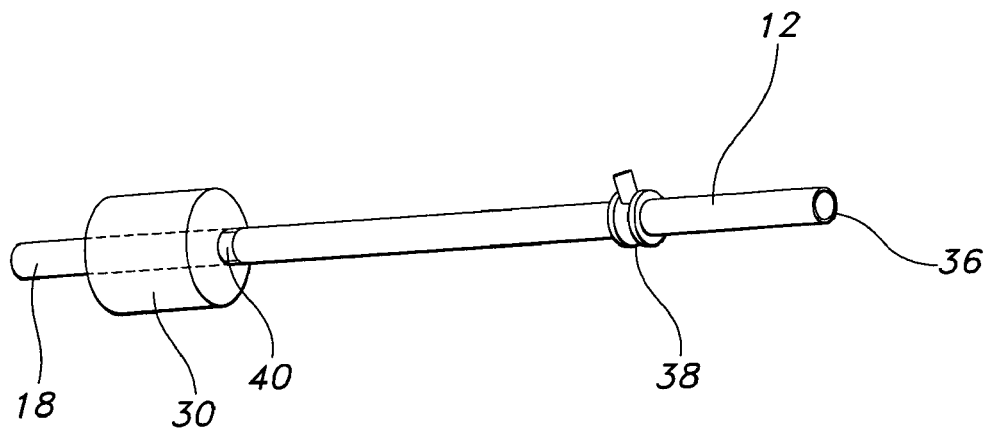
FIG. 2 is an isometric view of the FIG. 1 multilumen catheter in a straightened configuration.

Looking now to FIG. 2, a more detailed view of the tracheal tube 12 may be had. This view depicts the tube 12 in a straightened configuration. A collar 38 is positioned on the tube 12. The collar 38 rotates about the cannula and provides the user or medical personnel with an ability to select functionalities as explained in greater detail below. An inlet port 40 or a plurality of such inlet ports 40 is provided at desirable locations along the tube 12. In some embodiments, such inlet ports 40 are located above the balloon 30, i.e., between the balloon 30 and the proximal end 36. In other embodiments, a inlet port or inlet ports 40 are located below the balloon 30, i.e., between the balloon 30 and the distal end 18. Some embodiments may have inlet ports on each side of the balloon 30.

Figure 3:
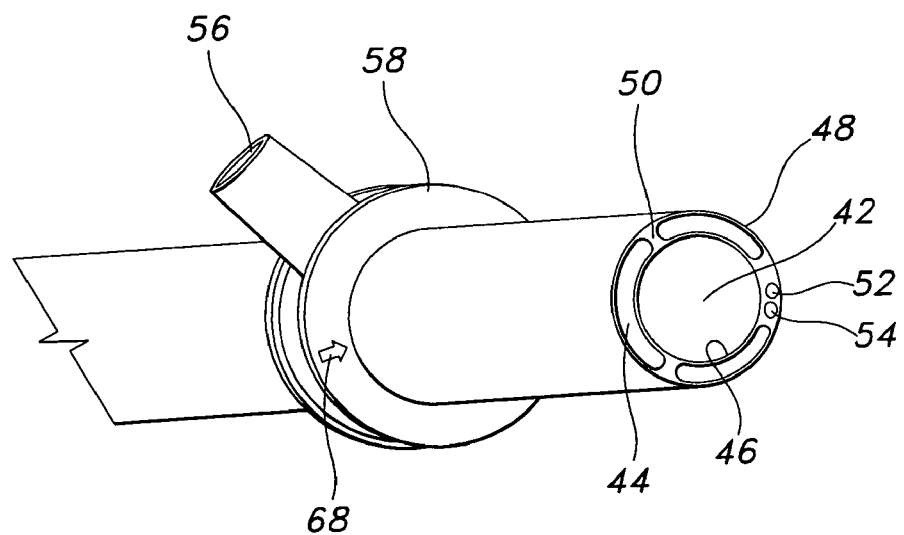
FIG. 3 is a cutaway of the FIG. 1 multilumen catheter viewed through the axial centerline of the multilumen catheter so as to depict the passages therethrough.

As shown in FIG. 3, the tube 12 is configured as a cannula with a plurality of internal lumens that extend at least partially along the length of the tube 12. In the FIG. 3 example, a ventilation lumen 42 is provided at the center of the tube 12. Surrounding the ventilation lumen 42 are a plurality of lumens, including at least one suction lumen 44. Many embodiments, such as the FIG. 3 embodiment contain a plurality of such suction lumens 44 arranged radially about the ventilation lumen 42. A first wall 46 separates the ventilation lumen 42 from the suction lumen 44. In this embodiment, a second wall 48 forms the exterior wall of the tube 12. A plurality of partitions 50 are provided to separate each suction lumen 44 from one another. Each of these walls and partitions may be created via extrusion of the material comprising the tube through an appropriate die during formation of the tube 12 and as such may effectively be considered as a single component having a plurality of lumens situated therein. In any event, the placement of lumens in a tracheal tube is a process that would be understood by those of skill in the art As seen in FIG. 3, additional lumens, such as an inflation lumen 52 and an irrigation lumen 54 may be provided. The inflation lumen 52 connects the balloon 30 to some means capable of inflating the balloon, thus keeping the tracheal tube 12 adequately sealed and positioned desirably within the trachea 16. An irrigation lumen 54 may also be provided to enable medical personnel to introduce a lavage solution or to medicate the patient 10. In some embodiments, one or more of the suction lumens 44 may alternatively be used as irrigation lumens. The collar 38 is provided with an outlet 56 which leads to a suction source (not shown). A guide 58 may also be provided within which the collar 38 is allowed to rotate.

Figure 4:
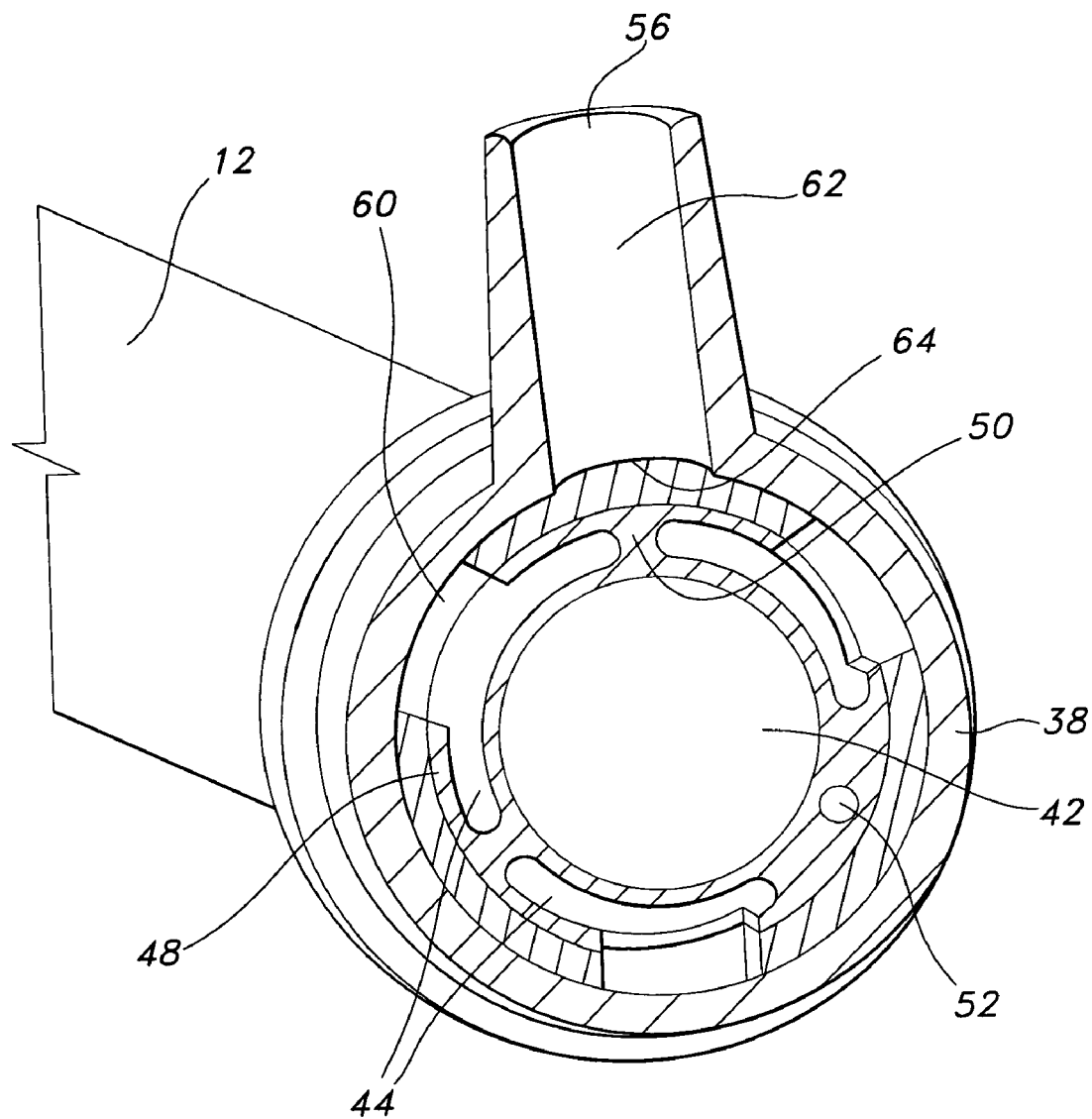
FIG. 4 is a cutaway of the FIG. 1 multilumen catheter viewed through the radial centerline of the multilumen catheter so as to depict one embodiment of the guide and collar.

Turning to FIG. 4, a partial cutaway view depicting the internal configuration of one embodiment of the collar 38 is shown. It may be seen that a plurality of suction lumens 44 are shown radially disposed about the ventilation lumen 42. The suction lumens 44, in this embodiment, three such lumens extend substantially around the entire cannula with the exception of a region containing the inflation lumen 52. Each suction lumen 44 contains a suction port 60 that extends through the tube wall or second wall 48. The collar 38 contains a passage or conduit 62 connecting the outlet 56 to an inlet 64. Rotating the collar 38 about the tube 12 enables the user or medical personnel to selectively align the inlet 64 within the collar 38 with a specific suction port 60 within a specific suction lumen 44. Of course each suction lumen 44 is provided with an inlet port 40 as described above as well as a suction port 60. By rotating the collar into the desired position, the user or medical personnel is provided with a selectable means with which to suction fluids from the patient 10.

The inlet 64 within the collar 38 may be configured so that it accesses more than one suction lumen 44 simultaneously. One manner with which to accommodate this configuration would be to place the suction ports 60 of adjacent lumens 44 proximate to the partitions 50 between the lumens 44. Alternatively, the partition 50 may be eliminated at the intersection of the adjacent suction ports 60. In any event, if the inlet 64 has access to more than one suction lumen 44 at a time, suction on more than one lumen may take place. Furthermore, the collar 38 may be capable of occluding all suction ports 60. This would effectively eliminate any suctioning capabilities.

Figure 5:
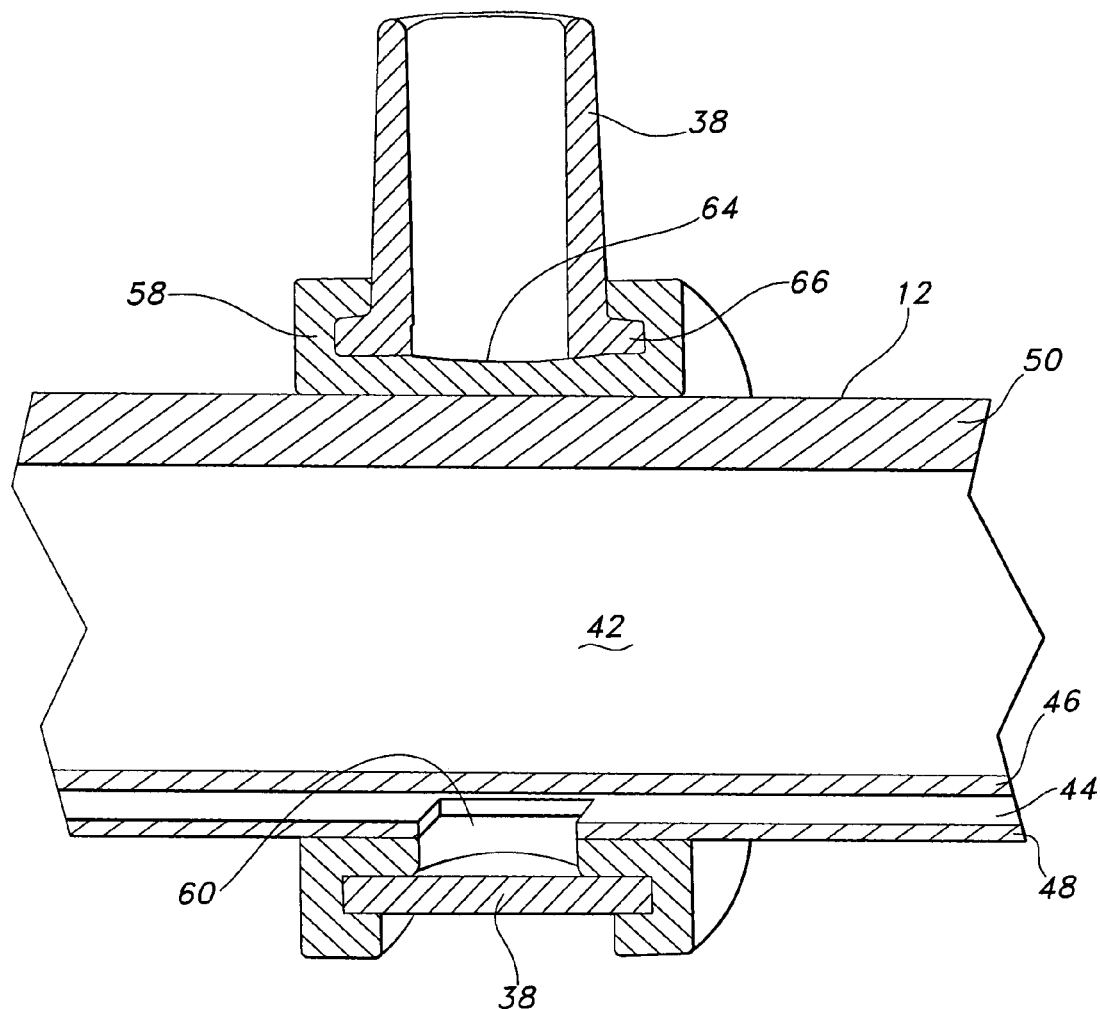
FIG. 5 is a side cutaway of the FIG. 1 multilumen catheter viewed through the radial centerline of the multilumen catheter, perpendicular to the FIG. 4 depiction, so as to depict the guide and collar.
Figure 6:
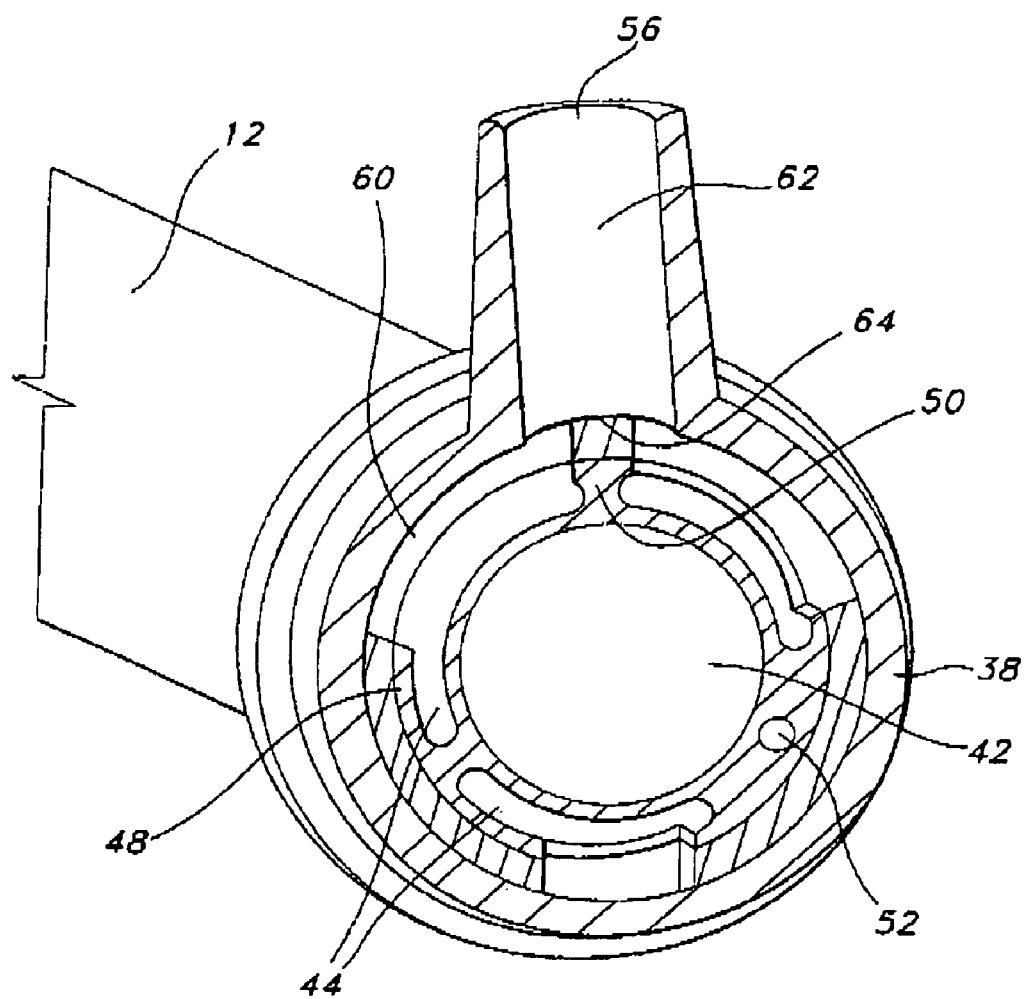
FIG. 6 is a cutaway of the FIG. 1 multilumen catheter viewed through the radial centerline of the multilumen catheter so as to depict one embodiment of the guide and collar where a suction port provides access to multiple suction lumens.

Looking finally to FIG. 5, a partial cutaway view normal to the FIG. 4 view depicts the internal configuration of one embodiment of the collar 38 for additional clarity. This view depicts the tube 12, the ventilation lumen 42, one suction lumen 44 separated from the ventilation lumen by the first wall 46 and bounded on the opposite side by second wall 48. One of the partitions 50 is depicted as well. The suction port 60 may be clearly seen as forming a passage through the second wall 48. In this view, the inlet 64 of the collar 38 is not aligned with the suction port 60 of lumen 44, therefore flow or suctioning would be prevented. It should be easy to envision that appropriate rotation of the tubular component forming the passage or conduit 62 to the suction port 60 would enable suctioning.

In this FIG., details with respect to the guide 58 as well as the collar 38 may be seen. In some embodiments, the guide 58 is secured to the tube 12 such that rotational movement of the guide with respect to the tube is prevented. Appropriate measures should be taken to ensure that the collar 38 is capable of rotation with respect to the guide 58. For example, a flanged interface 66 between the two components may be used. Such an interface should be fluid tight so as not to enable air leakage into the system when suctioning or to have fluid leakage from the system to the environment. As such, those skilled in the art would understand and be capable of providing an appropriate fluid tight seal to these areas.

During use, the collar 38 would be rotated to the desired suction lumen 44. An indicator 68, for example, such as the one depicted in FIG. 3 may be provided. An indicator would enable a user to appropriately align the passage or conduit 62 with a specific suction lumen. As such, an indicator may be provided which corresponds to each suction lumen. In lieu or in addition, the collar 38 may be made to incrementally click, lock, or snap into each suctioning position as well as a non-suctioning position. This may be accomplished by any number of means known to those with skill in the art. As can be seen from the FIGs., each suction lumen 44 may be used bi-directionally, that is, each suction lumen may be used to introduce a fluid into the patient. Some such fluids may comprise medicaments, lavage to clean the lumen or the patient's trachea, as well as other fluids.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A tracheal tube comprising:
 a tube having a first wall and a second wall concentric to the first wall, a first surface of the first wall surrounding and defining a ventilation lumen, the first wall being attached at a second surface to a first surface of the second wall at a plurality of partitions having surfaces, a plurality of suction lumens being defined by the second surface of the first wall, the first surface of the second wall, and the surfaces of adjacent partitions, a plurality of suction ports, each corresponding to a suction lumen and formed through a portion of the second wall;
 a suction port collar having an inlet and an outlet, the suction port collar surrounding the tube and overlapping the suction ports, the suction port collar being selectively positionable so as to enable fluid communication between the inlet and at least one suction port while occluding any remaining suction port, the outlet adapted to connect to a suction source;
 an inflatable cuff sealed to and surrounding the tube at a distal end adapted to seal the trachea of a patient, each suction lumen comprising an inlet port proximal to the inflatable cuff and terminating at the suction ports.

2. The tracheal tube of claim 1 wherein the suction port collar is rotatable about the tube.

3. The tracheal tube of claim 1 having a lumen selected from the group consisting of an inflation lumen and an irrigation lumen.

4. The tracheal tube of claim 1 where the plurality of suction lumens are disposed radially about the second surface of the first wall.

5. The tracheal tube of claim 1 comprising a guide coupled to the tube and disposed over each suction port, the guide having openings aligned with each suction port, the suction port collar rotationally attached to the guide.

6. The tracheal tube of claim 1 wherein the collar comprises a cylindrical ring having an inner diameter, an outer diameter, and a tubular conduit affixed substantially normal to a plane tangential to the outer diameter, the inlet being at that end of the conduit coincident with the inner diameter, and the outlet being at the opposite end of the conduit.

7. The tracheal tube of claim 1 wherein the inlet is capable of aligning with only a single suction port at any one point in time.

8. The tracheal tube of claim 1 wherein each suction port provides access to a plurality of suction lumens.

9. The tracheal tube of claim 1 wherein the suction port collar provides a fluid tight seal between the suction port collar and the tube enabling fluid passage only through the suction port selected.

10. The tracheal tube of claim 1 wherein the suction port collar selectively and simultaneously occludes all suction ports.

11. A tracheal tube comprising:
a plurality of suction lumens, each suction lumen comprising a suction port; and
a suction port collar comprising an outlet, the suction port collar overlapping each suction port, a portion of the suction port collar selectively occluding a plurality of the suction ports while enabling unimpeded passage between a remainder of the suction ports and the outlets;
an inflatable cuff sealed to and surrounding the cannula at a distal end adapted to seal the trachea of a patient, each suction lumen comprising an inlet port proximal to the inflatable cuff and terminating at the suction ports.

12. The tracheal tube of claim 11 comprising a ventilation lumen, the plurality of suction lumens being radially disposed about an outer diameter of the ventilation lumen.

13. The tracheal tube of claim 11 wherein each suction lumen comprises an inlet and an outlet, the suction lumen outlet corresponding to at least one of the suction ports.

14. The tracheal tube of claim 11 wherein the tube comprises a cannula having coaxially oriented lumens, an inner lumen comprising a ventilation lumen, an outer lumen being further divided by partitions into coaxially oriented lumens spaced about the inner lumen.

15. The tracheal tube of claim 11 wherein the tube comprises a cannula with the plurality of suction lumens disposed therein, each suction lumen being separated from another by a partition.

16. The tracheal tube of claim 15 wherein at least one suction port is intersected by one of the partitions such that the suction port accesses more than one suction lumen.

17. The tracheal tube of claim 15 wherein an interior surface of the suction port collar is rotationally affixed to an exterior surface of the cannula in a fluid tight manner, the suction port collar having a conduit disposed thereon, the conduit having a conduit inlet disposed upon the interior surface of the suction port collar, a conduit outlet, and forming a fluid path between the conduit inlet and the conduit outlet.

18. The tracheal tube of claim 15 comprising a guide affixed to an exterior surface of the cannula, the guide having openings therein corresponding to the suction ports, wherein an interior surface of the suction port collar is rotationally affixed to an exterior surface of the guide, and rotation of the suction port collar about the guide results in the selective occlusion of some of the suction ports.

* * * * *

UNITED STATES PATENT AND TRADEMARK OFFICE
CERTIFICATE OF CORRECTION

PATENT NO. : 7,581,541 B2 Page 1 of 1
APPLICATION NO. : 11/198994
DATED : September 1, 2009
INVENTOR(S) : Madsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this

Fourteenth Day of December, 2010

David J. Kappos
*Director of the United States Patent and Trademark Office*